US00PP31545P2

(12) United States Plant Patent
Hansen

(10) Patent No.: US PP31,545 P2
(45) Date of Patent: Mar. 10, 2020

(54) ***KNIPHOFIA* PLANT NAMED 'ORANGE BLAZE'**

(50) Latin Name: ***Kniphofia* hybrid**
Varietal Denomination: Orange Blaze

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/350,347

(22) Filed: Nov. 6, 2018

(51) Int. Cl.
*A01H 5/02* (2018.01)
*A01H 6/00* (2018.01)

(52) U.S. Cl.
USPC ..... Plt./443

(58) Field of Classification Search
USPC ..... Plt./443
CPC ..... A01H 6/00; A01H 5/02
See application file for complete search history.

*Primary Examiner* — Keith O. Robinson

(57) ABSTRACT

A new and distinct cultivar of Red Hot Poker plant named *Kniphofia* 'Orange Blaze' with long, upright to gracefully-arching, strap-like, keeled, glaucous, gray-green foliage and numerous scapes beginning in late spring and repeating for nine weeks into September in Michigan. Habit is densely growing, winter-hardy, resistant to lodging, heat, deer and rabbits. Numerous scapes of strong orange on medium tall scapes beginning in late spring and repeating repeating for nine weeks into mid-September. The new plant is useful for landscaping as a specimen, en masse, or as a long-lasting cut flower.

1 Drawing Sheet

Botanical classification: *Kniphofia* hybrid.
Variety denomination: 'Orange Blaze'.

BACKGROUND AND ORIGIN OF THE PLANT

The present invention relates to the new and distinct Red Hot Poker, *Kniphofia* 'Orange Blaze' hybridized under the direction of the inventor at a wholesale perennial nursery in Zeeland, Mich. USA on Aug. 17, 2012 and seed was collected in the fall of 2012. The new plant was a single seedling selection resulting from a cross of 'Papaya Popsicle' U.S. Plant Pat. No. 22,915 as the female parent or seed parent and 'Echo Rojo' U.S. Plant Pat. No. 22,791 as the male parent. The plant passed initial evaluation in the summer of 2014 and was subsequently given the breeder code 12-4-5 prior to naming. *Kniphofia* 'Orange Blaze' has been successfully asexually propagated by division method since 2014 at the same wholesale perennial nursery in Zeeland, Mich. and subsequently by shoot tip tissue culture, and both methods have been found to be stable and produce identical plants that maintain the unique characteristics of the original plant through multiple generations.

No plants of *Kniphofia* 'Orange Blaze' have been sold, in this country or anywhere in the world, with this name or any other name, prior to the filing of this application, nor has any disclosure of the new plant been made prior to the filing of this application except that which was disclosed within one year of the filing of this application and was either derived directly or indirectly from the inventor.

SUMMARY OF THE PLANT

*Kniphofia* 'Orange Blaze' differs from its parents as well as all other *Kniphofia* known to the applicant. The most similar known *Kniphofia* cultivars are: 'Redhot Popsicle' U.S. Plant Pat. No. 24,036, 'Poco Orange' U.S. Plant Pat. No. 27,677, 'Mango Popsicle' U.S. Plant Pat. No. 22,968, 'First Surprise' U.S. Plant Pat. No. 16,036 and 'Fire Glow' U.S. Plant Pat. No. 22,894. The female parent, 'Papaya Popsicle', has flowers and buds that are of a less orangish hue on shorter scapes with fewer flowers. The male parent 'Echo Rojo' flowers and buds with a more reddish hue on taller scapes with fewer flowers. The new plant has greater contrast between flower bud and open flower color than 'Redhot Popsicle' U.S. Plant Pat. No. 24,036, the flower color of 'Redhot Popsicle' has a more reddish hue and the flower scapes are much shorter. 'Poco Orange' is much shorter in scape height and the flower color is slightly different. 'Mango Popsicle' has shorter foilage, fewer flowers per stem, the flower corolla is smaller and the flowers are a more yellowish orange. 'First Surprise' is lighter orange in flower bud color and slightly more yellowish pink in open flower on shorter scapes. 'Fire Glow' is more reddish in flower and bud color the scapes are shorter. 'Echo Mango' U.S. Plant Pat. No. 21,706 has flowers of apricot with much shorter inflorescences and fewer flowers per peduncle.

*Kniphofia* 'Orange Blaze' differs from these above cultivars and all cultivars known to the inventor in that it has:

1. Gracefully upright to arching, strap-like, keeled, gray-green foliage.
2. Rapidly growing, medium-sized clumps with dense habit, winter-hardy, heat tolerant, rabbit and deer tolerant and lodging resistant.
3. Numerous spikes of strong orange flower buds with slightly lighter strong orange open flowers on medium height stems;
4. Flowering beginning the last week of spring and continuing for about nine weeks and occasionally into mid-September in Michigan.

BRIEF DESCRIPTION OF THE DRAWINGS

The photographs of *Kniphofia* 'Orange Blaze' demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
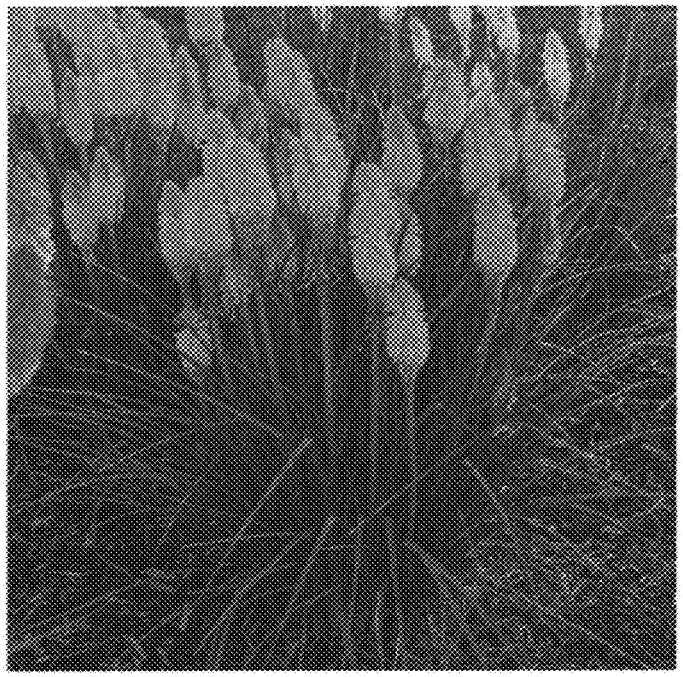
FIG. 1 shows the side-view habit of a five-year-old plant in midseason flowering.
Figure 2:
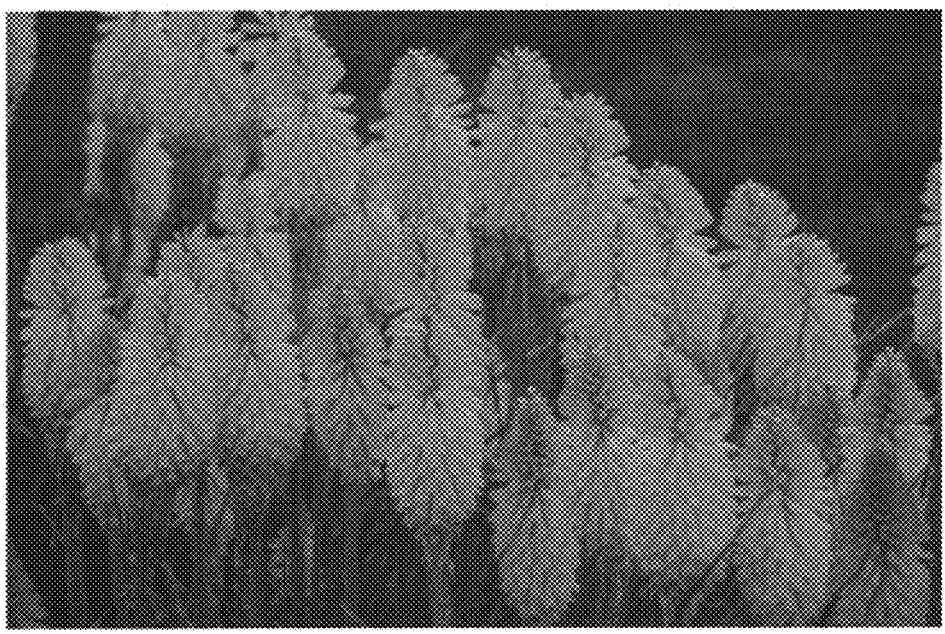
FIG. 2 shows a close-up of the flowers and buds.

The following descriptions and color references are based on the 2015 edition of The Royal Horticultural Society Colour Chart except where common dictionary terms are used. The new plant, *Kniphofia* 'Orange Blaze', has not been observed under all possible environments. The phenotype may vary slightly with different environmental conditions, such as temperature, light, fertility, moisture and maturity levels, but without any change in the genotype. The following observations and size descriptions are of a five-year-old plant in a trial garden of a wholesale perennial nursery in Zeeland, Mich. under full sun with supplemental water and fertilizer as needed.

Botanical classification: *Kniphofia* hybrid;

Parentage: *Kniphofia* 'Papaya Popsicle' as the female or seed parent and 'Echo Rojo' as the male or pollen parent;

Propagation method: By garden division of the crown and shoot tip tissue culture;

Growth rate: Vigorous, flowering in 3.5 liter containers in about 10 to 12 weeks from a 25 mm plug liner in late winter to spring and from a one-year-old bare root plant to flowering in 6 to 8 weeks in a 4.0 liter container;

Rooting habit: Fibrous from base of crown, lightly branching; color nearest RHS 158C;

Plant description: Dense, rhizomatous, acaulescent, perennial clump with long thin foliage to about 135.0 cm across and about 80.0 cm tall; flowering to about 77.0 cm tall; about 85 peduncles per plant;

Leaves: Linear; keeled at base, triangular in distal half; arranged about 8 leaves per basal division; apex narrowly acute; base sessile, truncate, clasping; margin entire, micro-dentate to fimbrillate; adaxial midrib micro-dentate; no fragrance observed;

Leaf size: To about 83.0 cm long and 15.0 mm across at base, average about 72.0 cm long and 14.0 mm across at base;

Leaf color: Young base nearest RHS 150D both abaxial and adaxial, nearest RHS 138A both abaxial and adaxial; mature adaxial nearest RHS 138A and abaxial nearest blend between RHS 138A and RHS N138B;

Leaf venation: Parallel; color nearest RHS 138A;

Stem: Acaulescent; crown about 18.0 mm across at base;

Inflorescence: In spike-like raceme; cylindrical; average about 160 flowers per stem; flowering portion to about 20.0 cm tall and about 6.0 cm across; lasting about three weeks; flower spacing less than 1.0 mm apart on raceme in distal region and about 2.5 cm in lowest flowers;

Peduncle: Cylindrical, solid not fistulose; glabrous; slightly glaucous; erect to about 77.0 cm long and about 10.0 mm diameter; average about 70.0 cm tall and about 9.0 mm diameter;

Peduncle color: Nearest blend between RHS 146D and RHS N144D;

Buds one day prior to opening: Ellipsoidal to tubular with slightly swollen subacute apex and rounded base; glabrous; lustrous; about 24.0 mm long and about 4.0 mm diameter at base and 6.5 mm diameter at widest point near apex; five days prior to anthesis about 20.0 mm long and 4.5 mm across;

Bud attitude: Beginning slightly upwardly and slightly drooping as maturing toward anthesis;

Bud color: One day prior to anthesis abaxial distal and dorsal portions nearest RHS 26A with tepal midrib nearest RHS N25B and base nearest RHS 21C; five days prior to anthesis distal tip nearest RHS N25A, middle portion nearest RHS 26A transitioning to nearest RHS 1C at base with veins same as surrounding tepal color;

Flowers: Fistulose, forming tubular corolla; perfect; actinomorphic; individually open and effective about three to four days; about 32.0 mm long and about 4.5 mm diameter at base;

Corolla size: To about 24.0 mm long, fused in basal about 22.0 mm; face to about 11.0 mm tall and about 9.5 mm wide; fused tube about 6.0 mm diameter near base;

Flower attitude: Drooping;

Flower fragrance: None detected;

Flowering period: Individual racemes effective for about 3 weeks; beginning the last week of spring and continuing for about nine weeks and occasionally into mid-September in Michigan;

Tepals: Six, in two sets of three; both sets with acute apices and fused in basal 22.0 mm forming tube; margin entire; glabrous and lustrous abaxial and adaxial; about 24.0 mm long and about 5.0 mm across just above fusion point;

Tepal color mature abaxial: Both inner and outer sets identically nearest RHS 26B with midribs nearest RHS 26A and tepal margins transparent to nearest RHS 18D; adaxial between RHS 26B and RHS 26C with midribs between RHS 26B and RHS 26A;

Androecium: Six; variable lengths;

*Filaments.*—Six; exserted; cylindrical; glabrous; lustrous; from about 24.0 to 29.0 mm long and about 0.5 mm diameter; color base nearest RHS 155C and distally nearest 4C.

*Anther.*—Dorsifixed; longitudinal, ellipsoidal; about 2.0 mm long and 1.5 mm across and 1.0 mm thick; color nearest RHS 13B.

*Pollen.*—Abundant: color nearest RHS 10A.

Gynoecium: Single; about 31.0 mm long; slightly exserted;

*Style.*—Terete; glabrous; lustrous; about 28.0 mm long and 0.7 mm diameter: color between RHS 14C and RHS 14D, nearest RHS 1B in proximal 1.0 mm proximal 1.0 mm nearest RHS 23C.

*Stigma.*—Flattened, round; about 0.3 mm across; color nearest RHS 19D.

*Ovary.*—Superior; globose; rounded apex, truncate base; about 3.5 mm long and 2.0 mm diameter; color nearest blend between RHS N144A and RHS 145A.

Pedicel: Cylindrical; glabrous; stiff; drooping; about 1.5 mm long and about 0.7 mm diameter;

Pedicel color: Nearest RHS 147D;

Bracts: Lanceolate; papery and translucent; at cauline nodes and subtending individual flowers; with acute apices and truncate base; to about 8.0 mm long and 3.0 mm across at base; decreasing distally; average about 7.0 mm long and 3.0 mm across; color blushed with nearest RHS 161D with midrib nearest RHS 177B;

Fruit: Tri-valved loculicidal capsule; ellipsoidal; about 8.0 mm long and 6.0 mm across; glabrous; with rounded apex and rounded base; typically six to twelve seeded; color upon maturity nearest RHS 200A;

Seed: Irregular with angular sides, acute apex and base; about 4.0 mm long and 3.0 mm across; color nearest RHS 200A;

Disease and pest resistance: 'Orange Blaze' is resistant to lodging of flower scapes, but further resistance beyond that of other *Kniphofia* has not been observed. The plant grows best with good drainage and is able to tolerate some heat when established. Hardiness at least from USDA zone 6 through 9 and 5b with protection.

I claim:

1. A new and distinct cultivar of Red Hot Poker plant named *Kniphofia* 'Orange Blaze' as herein described and illustrated.

* * * * *